United States Patent [19]

Denzel et al.

[11] 4,127,655
[45] Nov. 28, 1978

[54] 8H-PYRAZOLO[4′,3′:5,6]PYRIDO[3,4-E] [1,2,4]TRIAZOLO-[1,5-A]PYRIMIDINES

[75] Inventors: Theodor Denzel, Regensburg; Hans Hoehn, Tegernheim, both of Fed. Rep. of Germany

[73] Assignee: E. R. Squibb & Sons, Inc., Princeton, N.J.

[21] Appl. No.: 867,739

[22] Filed: Jan. 9, 1978

Related U.S. Application Data

[62] Division of Ser. No. 715,599, Aug. 18, 1976, Pat. No. 4,078,064.

[51] Int. Cl.² ............... C07D 471/22; A61K 31/535; A61K 31/505; A61K 31/54
[52] U.S. Cl. .................... 424/246; 424/248.5; 424/248.52; 424/248.54; 424/251; 424/248.4; 424/248.57; 544/58; 544/60; 544/115; 544/238; 544/247
[58] Field of Search .................... 544/58, 60, 115; 260/256.4 F, 256.5 R; 424/248.5, 248.52, 248.54, 248.56, 251, 246, 248.4, 248.57

[56] References Cited

U.S. PATENT DOCUMENTS 4,070,466  1/1978  Denzel .................. 544/115

Primary Examiner—Henry R. Jiles
Assistant Examiner—R. W. Ramsuer
Attorney, Agent, or Firm—Lawrence S. Levinson; Merele J. Smith

[57] ABSTRACT

New derivatives of 8H-pyrazolo[4′,3′:5,6]pyrido[3,4-e]-[1,2,4]triazolo[1,5-a]pyrimidine have the general formula

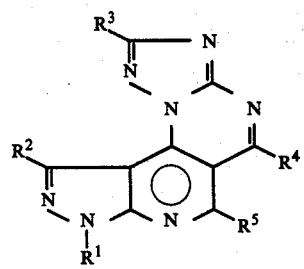

The compounds are useful as anti-inflammatory agents and central nervous system depressants.

8 Claims, No Drawings

8H-PYRAZOLO[4',3':5,6]PYRIDO[3,4-E][1,2,4]TRIAZOLO-[1,5-A]PYRIMIDINES

This is a division of application Ser. No. 715,599, filed Aug. 18, 1976, now U.S. Pat. No. 4,078,064.

SUMMARY OF THE INVENTION

This invention relates to new derivatives of 8H-pyrazolo[4',3':5,6]pyrido[3,4-e][1,2,4]triazolo[1,5-a]-pyrimidine and salts thereof. These new compounds have the general formula

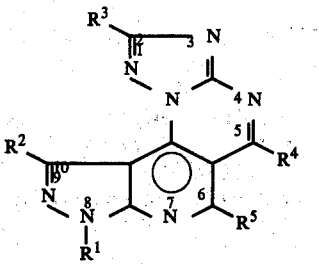

$R^1$ is hydrogen, lower alkyl, phenyl, phenyl-lower alkylene, benzoyl or substituted benzoyl.

$R^2$ is hydrogen, lower alkyl or phenyl.

$R^3$ is hydrogen, lower alkyl, phenyl, lower alkylthio or lower alkylsulfinyl.

$R^4$ is halo, lower alkoxy, the group

the group $-S-R^4$, substituted lower alkoxy wherein the substituent of the lower alkoxy is

phenyl-lower alkoxy, phenyloxy or substituted phenyloxy wherein the phenyl ring bears one or two simple substituents including lower alkyl, halogen or trifluoromethyl (preferably only one).

$R^5$ is hydrogen or lower alkyl.

$R^6$ is hydrogen, lower alkyl or substituted lower alkyl wherein the lower alkyl substituent is

phenyl or substituted phenyl wherein the phenyl substituent is halogen, lower alkyl or trifluoromethyl. $R^7$ is hydrogen or lower alkyl. When $R^6$ is substituted lower alkyl, $R^7$ is preferably hydrogen. In addition $R^6$ and $R^7$ together with the nitrogen may form an unsubstituted or substituted heterocyclic radical including pyrrolidino, morpholino, thiamorpholino, piperidino, pyrazolyl, dihydropyridazinyl or piperazinyl wherein the substituent on the heterocycle is lower alkyl or hydroxy-lower alkylene.

$R^8$, $R^9$ and $R^{10}$ each is hydrogen or lower alkyl.

DETAILED DESCRIPTION OF THE INVENTION

The various groups represented by the symbols are of the following types and have the same meanings throughout this specification:

The lower alkyl groups are straight or branched chain hydrocarbon groups having up to seven carbon atoms like methyl, ethyl, propyl, isopropyl, butyl, isobutyl, t-butyl, pentyl and the like. The lower alkylene groups are divalent radicals of the same kind. Examples of the phenyl-lower alkylene groups are benzyl, phenethyl, phenylisopropyl and the like. The $C_1$-$C_4$ and especially the $C_1$-$C_2$ lower alkyl and lower alkylene groups are preferred. The lower alkoxy, lower alkylthio and lower alkylsulfinyl groups are of the same type. The $C_1$-$C_4$ and $C_1$-$C_2$ groups are similarly preferred and especially preferred groups, respectively.

The substituted phenyloxy and substituted benzoyl groups (i.e., $R^{11}$-phenyloxy, $R^{11}$-benzoyl) are simply substituted groups bearing on the phenyl ring one or two (preferably one), halo, lower alkyl or trifluoromethyl substituents ($R^{11}$), for example, p-chlorophenyloxy, o-chlorophenyloxy, p-bromophenyloxy, m-chlorophenyloxy, m-bromophenyloxy, p-tolyloxy, o-tolyloxy, o-ethylphenyloxy, p-trifluoromethylphenyloxy, 3,4-dichlorophenyloxy, 3,5-dimethylphenyloxy, p-bromobenzoyl, m-bromobenzyl, 3,5-dichlorobenzoyl, p-methylbenzoyl, o-ethylbenzoyl, p-trifluoromethylbenzoyl and the like. Halo, especially chlorine and bromine, and lower alkyl, especially methyl, are the preferred substituents (only one) in both instances.

The halogens in each instance are the four common halogens but chlorine and bromine, especially chlorine, are preferred.

The amino groups

wherein $R^6$ and $R^7$ each represents hydrogen or lower alkyl include the amino group, lower alkylamino groups like methylamino, ethylamino, propylamino, isopropylamino, butylamino, etc., and di-lower alkylamino groups like dimethylamino, diethylamino, methylethylamino, dipropylamino, dibutylamino and the like (preferably, but not necessarily, both lower alkyl groups are the same in a given compound). $R^6$ and $R^7$ can also join with the nitrogen to form one of the heterocyclic radicals pyrrolidino, morpholino, thiamorpholino, piperidino, pyrazolyl, dihydropyridazinyl or piperazinyl. These heterocyclic radicals may be unsubstituted or substituted with a lower alkyl or hydroxy-lower alkylene group ($R^{12}$). The preferred heterocyclics are piperidino, morpholino and 4-methylpiperazino.

The substituted lower alkoxy groups represented by $R^4$ and the substituted lower alkyl groups represented by $R^6$ may bear an amino group

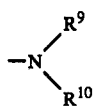

as described above resulting in $R^4$ substituents which are amino-lower alkoxy groups

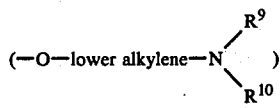

and amino-lower alkyleneamino groups

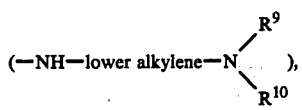

respectively, including, for example, aminoethoxy, aminopropoxy, methylaminoethoxy, ethylaminoethoxy, ethylaminopropoxy, dimethylaminoethoxy, dimethylaminopropoxy, diethylaminoethoxy, dimethylaminobutoxy, diethylaminopropoxy, aminoethylamino, aminopropylamino, methylaminopropylamino, ethylaminoethylamino, dimethylaminoethylamino, diethylaminoethylamino, dimethylaminopropylamino, and the like. Preferred are those groups wherein the lower alkyl and lower alkylene groups have up to 4 carbons, especially 2 to 3 carbons. Especially preferred groups of this type are di-lower alkylamino-lower alkoxy, especially dimethylaminoethoxy and di-lower alkylamino-lower alkyleneamino, especially dimethylaminopropylamino.

Preferred groups of compounds of formula I are those wherein $R^1$ is hydrogen or lower alkyl, especially the latter and most especially ethyl; $R^2$ is hydrogen or lower alkyl, especially hydrogen; $R^3$ is hydrogen, lower alkyl or lower alkylthio, especially hydrogen or methyl; $R^4$ is amino, mercapto, lower alkylthio, especially methylthio, lower alkylamino, especially $C_1$-$C_4$-lower alkylamino, lower alkoxy, especially $C_1$-$C_5$-lower alkoxy, di(lower alkyl)amino, especially $C_1$-$C_4$-di(lower alkyl)amino or di(lower alkyl)amino(lower alkoxy) or di(lower alkyl)amino-lower alkylamino. $R^5$ is hydrogen or lower alkyl, especially hydrogen.

The products of the examples are representative of the various compounds of this invention and constitute especially preferred embodiments.

The new compounds of formula I are formed by the following series of reactions. The symbols in the structural formulas have the same meaning as previously described.

A 4-hydrazinopyrazolo[3,4-b]pyridine of the formula

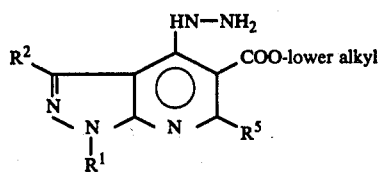

(produced according to the procedure given in U.S. Pat. No. 3,761,487, Sept. 25, 1973) is made to react with a lower alkoxymethylene cyanamide of the formula

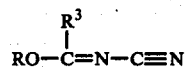

or a lower alkylthiomethylene cyanamide of the formula

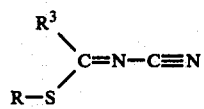

wherein R in both formulas is lower alkyl, in a high boiling alcohol like n-butyl alcohol or n-amyl alcohol or dioxane or the like, at about reflux temperature.

By this reaction is obtained a compound of the formula

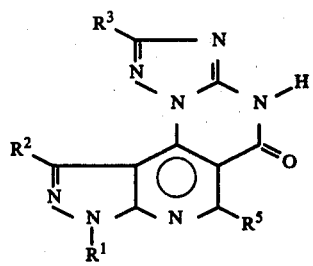

For additional details with respect to the production of compounds of formula V, reference is made to our copending application Ser. No. 704,855 filed July 13, 1976.

Reaction of the compound of formula V with a chlorinating agent, like phosphorus oxychloride or phosphorus pentachloride, results in the formation of a compound of the formula

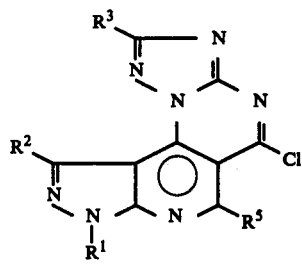

Compounds of formula I wherein $R^4$ is lower alkoxy or amino-lower alkoxy are now produced by reaction of the compound of formula VI with an alcoholate of the formula

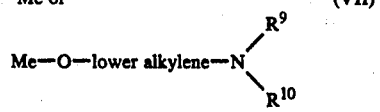

wherein Me is an alkali metal like sodium or potassium.

When $R^3$ is lower alkylsulfinyl, the compound of formula V wherein $R^3$ is lower alkylthio is first formed, e.g., by reaction of the compound of formula II with the compound of formula IV wherein $R^3$ is lower alkylthio. This product is oxidized, e.g., with an alkali metal periodate like sodium metaperiodate and then further processed as described above.

Compounds of formula I wherein $R^4$ is lower alkylthio are obtained by reaction of a compound of formula VI with an alkali metal mercaptide of the formula

     (VIII)

wherein Me is again an alkali metal like sodium or potassium and $R^8$ is lower alkyl. Compounds of formula I wherein $R^4$ is mercapto are obtained by reaction of a compound of formula VI with an alkali metal sulfide like sodium sulfide. Compounds of formula I wherein $R^4$ is an amino group or amino-lower alkylene group are produced by reaction of a compound of formula VII with an amine of the formula

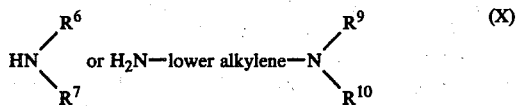     (X)

at elevated temperatures.

The new compounds of formula I form salts which are also part of this invention. The salts include acid addition salts, particularly the non-toxic, physiologically acceptable members. These salts are formed by reaction with one or more equivalents of a variety of inorganic and organic acids providing acid addition salts, including, for example, hydrohalides (especially hydrochloride and hydrobromide), sulfate, nitrate, borate, phosphate, oxalate, tartrate, maleate, citrate, acetate, ascorbate, succinate, aryl- and alkanesulfonates like benzenesulfonate, methanesulfonate, cyclohexanesulfamate and toluenesulfonate, etc. The acid addition salts frequently provide a convenient means for isolating the product, e.g., by forming and precipitating a salt (which is not necessarily non-toxic) in an appropriate medium in which the salt is insoluble, then after separation of the salt, neutralizing with a base such as barium hydroxide or sodium hydroxide, to obtain the free base of formula I. Other salts can then be formed from the free base by reaction with an equivalent or more of acid containing the desired anion.

The new compounds of this invention have antiinflammatory properties and are useful as anti-inflammatory agents, for example, to reduce local inflammatory conditions such as those of an edematous nature or resulting from proliferation of connective tissue in various mammalian species such as rats, dogs and the like when given orally in dosages of about 1 to 50 mg/kg/day, preferably 2 to 15 mg/kg/day, in single or 2 to 4 divided doses, as indicated by the carageenan edema or delayed hypersensitivity skin reaction tests in rats. They can also be used topically.

The new compounds of this invention also have central nervous system depressant activity and can be used as psychotropic agents, e.g., as ataractic agents for the relief of anxiety and tension states, for example, in mice, cats, rats, dogs and other mammalian species. For this purpose a compound or mixture of compounds of formula I, or non-toxic, physiologically acceptable acid addition salt thereof, is preferably administered orally, but parenteral routes such as subcutaneously, intramuscularly, intravenously or intraperitoneally in the described dosages, can also be employed. A single dose, or preferably 2 to 4 divided daily doses, provided on a basis of about 5 to 50 mg/kg/day, preferably about 10 to 25 mg/kg/day, is appropriate.

The compounds of the invention can be utilized by formulation in compositions such as tablets, capsules or elixirs for oral administration or in sterile solutions or suspensions for parenteral administration. About 10 to 300 mg of a compound or mixture of compounds of formula I or physiologically acceptable acid addition salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as dicalcium phosphate, a disintegrating agent such as corn starch, potato starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup or elixir may contain the active compound, sucrose as a sweetening agent, methyl and propyl parabens as preservatives, a dye and a flavoring such as cherry or orange flavor.

For topical administration as an anti-inflammatory agent, a conventional lotion, ointment or cream containing about 0.1 to 3 percent by weight of a compound of formula I or its salt is formulated.

The following examples are illustrative of the invention and constitute especially preferred embodiments. They also serve as models for the preparation of other members of the group which can be produced by suitable substitution of starting materials. All temperatures are in degrees celsius.

EXAMPLE 1

N-[3-(Dimethylamino)propyl]-8-ethyl-8H-pyrazolo[4',3':5,6]-pyrido[3,4-e][1,2,4]triazolo[1,5-a]pyrimidin-5-amine (a)

8-Ethyl-4H-pyrazolo[4',3':5,6]pyrido[3,4-e][1,2,4]-triazolo[1,5-a]pyrimidin-5(8H)-one 249 g. of 1-ethyl-4-hydrazino-1H-pyrazolo[3,4-b]-pyridine-5-carboxylic acid, ethyl ester (1 mol.) are refluxed in 1.5 liters of dry dioxane together with 98 g. of ethoxymethylene cyanamide for 12 hours. After cooling to room temperature, the precipitated 8-ethyl-4H-pyrazolo[4',3':5,6]pyrido[3,4-e][1,2,4]triazolo[1,5-a]-pyrimidin-5(8H)-one is filtered off and recrystallized from dimethylformanide, yield 135 g. (53%); m.p. 355°–356°.

(b)

5-Chloro-8-ethyl-8H-pyrazolo[4',3':5,6]pyrido[3,4-e][1,2,4]-triazolo[1,5-a]pyrimidine 25.5 g. of 8-ethyl-4H-pyrazolo[4',3':5,6]pyrido[3,4-e]-[1,2,4]triazolo[1,5-a]pyrimidin-5(8H)-one (0.1 mol.) are refluxed in 100 ml. of phosphorus oxychloride for 12 hours. After this time, the excess phosphorus oxychloride is distilled off in vacuo, the residue is treated with dry acetone and filtered off. 25 g. of 5-chloro-8-ethyl-8H-pyrazolo[4',3':5,6]pyrido[3,4-e][1,2,4]triazolo[1,5-a]pyrimidine are obtained, yield 92%; m.p. 196°–197°.

(c)

N-[3-(Dimethylamino)propyl]-8-ethyl-8H-pyrazolo-[4',3':5,6]pyrido[3,4-e][1,2,4]triazolo[1,5-a]pyrimidin-5-amine 2.7 g. of 5-chloro-8-ethyl-8H-pyrazolo[4',3':5,6]pyrido[3,4-e][1,2,4]triazolo[1,5-a]pyrimidine are treated with 5 g. of 3-dimethylaminopropylamine with stirring at 80° for 1 hour. The excess amine is removed in vacuo and the residue dissolved in hot ethyl acetate. The solution is filtered and the N-[3-(dimethylamino)propyl]-8-ethyl-8H-pyrazolo[4',3':5,6]pyrido[3,4-e][1,2,4]triazolo[1,5-a]-pyrimidin-5-amine precipitates on cooling, yield 2.8 g. (83%); m.p. 190°–192°. Treating the product with ethanolic HCl yields the hydrochloride salt.

EXAMPLE 2

8-Ethyl-N-(1-methylpropyl)-8H-pyrazolo[4',3':5,6-]pyrido-[3,4-e][1,2,4]triazolo[1,5-a]pyrimidin-5-amine By substituting 1-methylpropylamine for the 3-dimethylaminopropylamine in the procedure of Example 1 (c), 8-ethyl-N-(1-methylpropyl)-8H-pyrazolo[4',3':5,6-]pyrido[3,4-e]-[1,2,4]triazolo[1,5-a]pyrimidin-5-amine is obtained, yield 78%; m.p. 228°–230° (methanol).

EXAMPLE 3

N,N-8-Triethyl-8H-pyrazolo[4',3':5,6]pyrido[3,4-e][1,2,4]-triazolo[1,5-a]pyrimidin-5-amine By substituting diethylamine for the 3-dimethylaminopropylamine in the procedure of Example 1 (c), N,N-8-triethyl-8H-pyrazolo[4',3':5,6]pyrido[3,4-e][1,2,4]triazolo[1,5-a]-pyrimidin-5-amine is formed, yield 71%; m.p. 215°–217° (ethyl acetate).

EXAMPLE 4

5-Ethoxy-8-ethyl-8H-pyrazolo[4',3':5,6]pyrido[3,4-e][1,2,4]-triazolo[1,5-a]pyrimidine 2.7 g. of 5-chloro-8-ethyl-8H-pyrazolo[4',3':5,6]pyrido[3,4-e][1,2,4]triazolo[1,5-a]pyrimidine of Example 1 (b) (0.01 mol.) are added with stirring to a solution of 2.3 g. of sodium in 50 ml. of dry ethanol. The mixture is stirred at room temperature for 6 hours. The precipitate is filtered off, washed with water and recrystallized from ethanol to obtain 5-ethoxy-8-ethyl-8H-pyrazolo[4',3':5,6]pyrido[3,4-e]-[1,2,4]triazolo[1,5-a]pyrimidine, yield 2.1 g. (74%); m.p. 196°–197°.

EXAMPLE 5

8-Ethyl-5-methoxy-8H-pyrazolo[4',3':5,6]pyrido[3,4-e][1,2,4]-triazolo[1,5-a]pyrimidine 5-Chloro-8-ethyl-8H-pyrazolo[4',3':5,6]pyrido-[3,4-e][1,2,4]triazolo[1,5-a]pyrimidine of Example 1 (b) is treated with sodium methoxide in methanol as described in Example 4 to obtain 8-ethyl-5-methoxy-8H-pyrazolo[4',3':5,6]-pyrido[3,4-e][1,2,4]triazolo[1,5-a]pyrimidin-5-amine, yield 68%; m.p. 215°–216° (alcohol).

EXAMPLE 6

5-Butoxy-8-ethyl-8H-pyrazolo[4',3':5,6]pyrido[3,4-e][1,2,4]-triazolo[1,5-a]pyrimidine By substituting butyl alcohol for ethanol in Example 4, 5-butoxy-8-ethyl-8H-pyrazolo[4',3':5,6]pyrido[3,4-e][1,2,4]-triazolo[1,5-a]pyrimidine is obtained, yield 81%; m.p. 140°–142° (butanol).

EXAMPLE 7

5-[2-(Dimethylamino)ethoxy]-8-ethyl-8H-pyrazolo[4',3':5,6]-pyrido[3,4-e][1,2,4]triazolo[1,5-a]pyrimidine 8.9 g. of 2-dimethylaminoethanol are dissolved in 200 ml. of anhydrous benzene. To this solution a corresponding amount of butyl-lithium in hexane is added with stirring. After 1 hour, 5.5 g. of 5-chloro-8-ethyl-8H-pyrazolo-[4',3':5,6]pyrido[3,4-e][1,2,4]triazolo[1,5-a]pyrimidine of Example 1 (b) are added and the mixture is refluxed with stirring for 12 hours. The solvent is distilled off in vacuo and the residue is treated with 5 ml. of water and filtered off. Recrystallization from ethyl acetate yields 4.5 g. of 5-[2-(dimethylamino)ethoxy]-8-ethyl-8H-pyrazolo-[4',3':5,6]pyrido[3,4-e][1,2,4]triazolo[1,5-a]pyrimidine; m.p. 149°–150°.

EXAMPLE 8

8-Ethyl-5-(3-methylbutoxy)-8H-pyrazolo[4',3':5,6-]pyrido-[3,4-e][1,2,4]triazolo[1,5-a]pyrimidine By substituting 3-methylbutanol for the 2-dimethylaminoethanol in the procedure of Example 7, 8-ethyl-5-(3-methylbutoxy)-8H-pyrazolo[4',3':5,6-]pyrido[3,4-e]-[1,2,4]triazolo[1,5-a]pyrimidine is obtained, yield 68%; m.p. 140°–142°.

EXAMPLE 9

8-Ethyl-5-methylthio-8H-pyrazolo[4',3':5,6]pyrido[3,4-e]-[1,2,4]triazolo[1,5-a]pyrimidine 2.7 g. of 5-chloro-8-ethyl-8H-pyrazolo[4',3':5,6]-pyrido[3,4-e][1,2,4]triazolo[1,5-a]pyrimidine are treated with 1.5 g. of sodium methylmercaptide in 30 ml. of dimethylformamide with stirring at 80° for 5 hours. After this time, 10 ml. of water are added and the precipitate, 8-ethyl-5-methylthio-8H-pyrazolo[4',3':5,6-]pyrido-[3,4-e][1,2,4]triazolo[1,5-a]pyrimidine, is filtered off, yield 2.2 g. (77%); m.p. 198°–200° (butanol).

EXAMPLE 10

8-Ethyl-5-ethoxy-2-methylthio-8H-pyrazolo[4',3':5,6-]pyrido-[3,4-e][1,2,4]triazolo[1,5-a]pyrimidine (a)

8-Ethyl-2-methylthio-4H-pyrazolo[4',3':5,6]pyrido-[3,4-e][1,2,4]triazolo[1,5-a]pyrimidin-5(8H)-one 24.9 g. of 1-ethyl-4-hydrazino-1H-pyrazolo[3,4-b]-pyridine-5-carboxylic acid, ethyl ester (0.1 mol.) are heated in 200 ml. of butyl alcohol with 11.5 g. of di(methylmercapto)methyl-methylene cyanamide for 10 hours. The solution is cooled to room temperature and the precipitated 8-ethyl-2-methylthio-4H-pyrazolo[4',3':5,6]-pyrido[3,4-e][1,2,4]triazolo[1,5-a]pyrimidin-5(8H)-one is filtered off, yield 14.0 g. (46%); m.p. > 300° (DMF).

(b)

8-Ethyl-5-ethoxy-2-methylthio-8H-pyrazolo[4',3':5,6-]pyrido[3,4-e][1,2,4]triazolo[1,5-a]pyrimidine

14 g. of 8-ethyl-2-methylthio-4H-pyrazolo[4',3':5,6]-pyrido[3,4-e][1,2,4]triazolo[1,5-a]pyrimidin-5(8H)-one are treated with 50 ml. of phosphorus oxychloride at 80° for 24 hours. The excess phosphorus oxychloride is distilled off and the residue carefully treated with 100 ml. of alcohol. After evaporation of the alcohol, the remaining 8-ethyl-5-ethoxy-2-methylthio-8H-pyrazolo[4',3':5,6]-pyrido[3,4-e][1,2,4]triazolo[1,5-a]pyrimidine is recrystallized from dimethylformamide, yield 53%; m.p. 209°–211°.

EXAMPLE 11

8-Ethyl-5-ethoxy-2-methylsulfinyl-8H-pyrazolo[4',3,:5,6]-pyrido[3,4-e][1,2,4]triazolo[1,5-a]pyrimidine

(a)

8-Ethyl-2-methylsulfinyl-4H-pyrazolo[4',3':5,6]pyrido-[3,4-e][1,2,4]triazolo[1,5-a]pyrimidin-5(8H)-one

3.01 g. of 8-ethyl-2-methylthio-4H-pyrazolo[4',3':5,6]-pyrido[3,4-e][1,2,4]triazolo[1,5-a]pyrimidin-5(8H)-one obtained in Example 10 (a) are oxidized with 2.2 g. of sodium metaperiodate in aqueous alcohol for 7 days at room temperature. The precipitate of 8-ethyl-2-methylsulfinyl-4H-pyrazolo[4',3':5,6-]pyrido[3,4-e][1,2,4]triazolo[1,5-a]pyrimidin-5(8H)-one is filtered off, washed with water and recrystallized from dimethylformamide, yield 2.8 g. (88%); m.p. > 300°.

(b)

8-Ethyl-5-ethoxy-2-methylsulfinyl-8H-pyrazolo[4',3':5,6]-pyrido[3,4-e][1,2,4]triazolo[1,5-a]pyrimidine

By substituting the product of part a in the procedure of Example 10 (b), 8-ethyl-5-ethoxy-2-methylsulfinyl-8H-pyrazolo[4',3':5,6]pyrido[3,4-e][1,2,4]triazolo[1,5-a]pyrimidine is obtained.

EXAMPLE 12

8-Ethyl-N-methyl-8H-pyrazolo[4',3':5,6]pyrido[3,4-e]-[1,2,4]triazolo[1,5-a]pyrimidin-5-amine

By substituting methylamine for the 3-dimethylaminopropylamine in the procedure of Example 1 (c), 8-ethyl-N-methyl-8H-pyrazolo[4',3':5,6]pyrido[3,4-e][1,2,4]-triazolo-[1,5-a]pyrimidin-5-amine is obtained, m.p. > 300°.

EXAMPLE 13

8-Ethyl-5-(1-piperidinyl)-8H-pyrazolo[4',3':5,6]pyrido-[3,4-e][1,2,4]triazolo[1,5-a]pyrimidine

By substituting piperidine for the 3-dimethylaminopropylamine in Example 1 (c), 8-ethyl-5-(1-piperidinyl)-8H-pyrazolo[4',3':5,6]pyrido[3,4-e][1,2,4]triazolo[1,5-a]pyrimidine is obtained.

EXAMPLE 14

N-[2-(Diethylamino)ethyl]-8-ethyl-8H-pyrazolo[4',3':5,6]pyrido[3,4-e][1,2,4]triazolo[1,5-a]pyrimidin-5-amine

By substituting for the (3-dimethylamino)propylamine in Example 1 (c) the equivalent amount of 2-(diethylamino)ethylamine, N-[2-(diethylamino)ethyl]-8-ethyl-8H-pyrazolo[4',3':5,6]-pyrido[3,4-e][1,2,4]triazolo[1,5-a]pyrimidin-5-amine is obtained.

EXAMPLE 15

5-Methoxy-8H-pyrazolo[4',3':5,6]pyrido[3,4-e][1,2,4]triazolo-[1,5-a]pyrimidine

By substituting an equivalent amount of 4-hydrazino-1H-pyrazolo[3,4-b]pyridine-5-carboxylic acid, ethyl ester for the 1-ethyl-4-hydrazino-1H-pyrazolo[3,4-b]pyridine-5-carboxylic acid, ethyl ester in the procedure of Example 1 (a), (b) then continuing as in Example 4 but substituting methanol for ethanol, 4H-pyrazolo[4',3':5,6]pyrido[3,4-e][1,2,4]-triazolo[1,5-a]pyrimidin-5(8H)-one, 5-chloro-8H-pyrazolo[4',3':5,6-]pyrido[3,4-e][1,2,4]triazolo[1,5-a]pyrimidine and 5-methoxy-8H-pyrazolo[4',3':5,6]pyrido[3,4-e][1,2,4]-triazolo[1,5-a]pyrimidine, respectively, are obtained.

EXAMPLE 16

5-Phenylmethoxy-8H-pyrazolo[4',3':5,6]pyrido[3,4-e][1,2,4]-triazolo[1,5-a]pyrimidine

By substituting the 5-chloro-8H-pyrazolo[4',3':5,6]-pyrido[3,4-e][1,2,4]triazolo[1,5-a]pyrimidine of Example 15 for the 5-chloro-8-ethyl-8H-pyrazolo[4',3':5,6-]pyrido-[3,4-e][1,2,4]triazolo[1,5-a]pyrimidine and benzyl alcohol for the ethanol in the procedure of Example 4, 5-phenyl-methoxy-8H-pyrazolo[4',3':5,6]pyrido[3,4-e][1,2,4]triazolo[1,5-a]pyrimidine is obtained.

EXAMPLE 17

8-Ethyl-5-(2-phenylethoxy)-8H-pyrazolo[4',3':5,6-]pyrido-[3,4-e][1,2,4]triazolo[1,5-a]pyrimidine

By substituting phenylethyl alcohol for the ethanol in the procedure of Example 4, 8-ethyl-5-(2-phenylethoxy)-8H-pyrazolo[4',3':5,6]pyrido[3,4-e][1,2,4]triazolo[1,5-a]-pyrimidine is obtained.

EXAMPLE 18

5-Phenyloxy-8,10-dimethyl-8H-pyrazolo[4',3':5,6-]pyrido-[3,4-e][1,2,4]triazolo[1,5-a]pyrimidine

By substituting 1,3-dimethyl-4-hydrazino-1H-pyrazolo[3,4-b]pyridine-5-carboxylic acid, ethyl ester for the 1-ethyl-4-hydrazino-1H-pyrazolo[3,4-b]pyridine-5-carboxylic acid, ethyl ester in the procedure of Example 1 and proceeding as in Example 4, but substituting phenol for the ethanol, 8,10-dimethyl-4H-pyrazolo[4',3':5,6]-pyrido[3,4-e][1,2,4]triazolo[1,5-a]pyrimidin-5(8H)-one, 5-chloro-8,10-dimethyl-8H-pyrazolo[4',3':5,6]pyrido[3,4-e]-[1,2,4]triazolo[1,5-a]pyrimidine and 5-phenyloxy-8,10-dimethyl-8H-pyrazolo[4',3':5,6]pyrido[3,4-e][1,2,4]triazolo-[1,5-a]pyrimidine, respectively, are obtained.

EXAMPLE 19

2-Ethyl-8-isopropyl-5-morpholino-8H-pyrazolo[4',3':5,6]-pyrido[3,4-e][1,2,4]triazolo[1,5-a]pyrimidine

By substituting 1-isopropyl-4-hydrazino-1H-pyrazolo-[3,4-b]pyridine-5-carboxylic acid, ethyl ester for the 1-ethyl-4-hydrazino-1H-pyrazolo[3,4-b]pyridine-5-carboxylic acid, ethyl ester and 1-ethoxypropylidene cyanamide for the ethoxymethylene cyanamide in part a and morpholine for the 3-dimethylaminopropylamine in part (c) of the procedure of Example 1, 2-ethyl-8-isopropyl-4H-pyrazolo-[4',3':5,6]pyrido[3,4-e][1,2,4]triazolo[1,5-a]pyridimin-5(8H)-one, 5-chloro-2- ethyl-8-isopropyl-8H-pyrazolo[4',3':5,6]-pyrido[3,4-e][1,2,4]triazolo[1,5-a]pyrimidine and 2-ethyl-8-isopropyl-5-morpholino-8H-pyrazolo[4',3':5,6]pyrido[3,4-e]-[1,2,4]triazolo[1,5-a]pyrimidine, respectively, are obtained.

EXAMPLE 20

5-(4-Chlorophenyloxy)-10-ethyl-8H-pyrazolo[4',3':5,6]-pyrido[3,4-e][1,2,4]triazolo[1,5-a]pyrimidine By substituting 3-ethyl-4-hydrazino-1H-pyrazolo[3,4-b]-pyridine-5-carboxylic acid propyl ester for the 1-ethyl-4-hydrazino-1H-pyrazolo[3,4-b]pyridine-5-carboxylic acid, ethyl ester in the procedure of Example 1 (a), (b) and then following the procedure of Example 4 but substituting 4-chlorophenol for the ethanol, 10-ethyl-4H-pyrazolo[4',3':5,6]-pyrido[3,4-e][1,2,4]triazolo[1,5-a]pyrimidin-5(8H)-one, 5-chloro-10-ethyl-8H-pyrazolo[4',3':5,6]pyrido[3,4-e]-[1,2,4]triazolo[1,5-a]pyrimidine and 5-(4-chlorophenyloxy)-10-ethyl-8H-pyrazolo[4',3':5,6]pyrido[3,4-e][1,2,4]-triazolo[1,5-a]pyrimidine, respectively, are obtained.

EXAMPLE 21

5-(3-methylphenyloxy)-8-phenyl-8H-pyrazolo[4',3':5,6-]pyrido-[3,4-e][1,2,4]triazolo[1,5-a]pyrimidine By substituting 4-hydrazino-1-phenyl-1H-pyrazolo-[3,4-b]pyridine-5-carboxylic acid, ethyl ester for the 1-ethyl-4-hydrazino-1H-pyrazolo[3,4-b]pyridine-5-carboxylic acid, ethyl ester in the procedure of Example 1 (a), (b), then proceeding as in Example 4 but substituting 3-methylphenol for the ethanol, 8-phenyl-4H-pyrazolo[4',3':5,6]pyrido-[3,4-e][1,2,4]triazolo[1,5-a]pyrimidin-5(8H)-one, 5-chloro-8-phenyl-8H-pyrazolo[4',3':5,6]pyrido[3,4-e][1,2,4]triazolo-[1,5-a]pyrimidine and 5-(3-methylphenyloxy)-8-phenyl-8H-pyrazolo[4',3':5,6]pyrido[3,4-e][1,2,4]triazolo[1,5-a]-pyrimidine, respectively, are obtained.

EXAMPLE 22

N-[2-(Diethylamino)ethyl]-8-ethyl-6-methyl-8H-pyrazolo-[4',3':5,6]pyrido[3,4-e][1,2,4]triazolo[1,5-a]pyrimidin-5-amine By substituting 1-ethyl-4-hydrazino-6-methyl-1H-pyrazolo[3,4-b]pyridine-5-carboxylic acid, ethyl ester for the 1-ethyl-4-hydrazino-1H-pyrazolo[3,4-b]pyridine-5-carboxylic acid, ethyl ester in part (a) and 2-diethyl-aminoethylamine for the 3-dimethylaminopropylamine in part c of the procedure of Example 1 8-ethyl-6-methyl-4H-pyrazolo[4',3':5,6]pyrido[3,4-e][1,2,4]triazolo-[1,5-a]pyrimidin-5(8H)-one, 5-chloro-8-ethyl-6-methyl-8H-pyrazolo[4',3':5,6]pyrido[3,4-e][1,2,4]triazolo[1,5-a]-pyrimidine and N-[2-(diethylamino)ethyl]-8-ethyl-6-methyl-8H-pyrazolo[4',3':5,6]pyrido[3,4-e][1,2,4]triazolo[1,5-a]-pyrimidin-5-amine, respectively, are obtained.

EXAMPLE 23

8-Benzyl-N-(1-methylpropyl)-8H-pyrazolo[4',3':5,6-]pyrido-[3,4-e][1,2,4]triazolo[1,5-a]pyrimidin-5-amine By substituting 1-benzyl-4-hydrazino-1H-pyrazolo-[3,4-b]pyridine-5-carboxylic acid, ethyl ester for the 1-ethyl-4-hydrazino-1H-pyrazolo[3,4-b]pyridine-5-carboxylic acid, ethyl ester in the procedure of Example 1 (a), (b) then proceeding as in Example 2, 8-benzyl-4H-pyrazolo[4',3':5,6]pyrido[3,4-e][1,2,4]triazolo[1,5-a]pyrimidin-5(8H)-one and 8-benzyl-5-chloro-8H-pyrazolo[4',3':5,6]pyrido[3,4-e]-[1,2,4]triazolo[1,5-a]pyrimidine and 8-benzyl-N-(1-methyl-propyl)-8H-pyrazolo[4',3':5,6]pyrido[3,4-e][1,2,4]triazolo-[1,5-a]pyrimidin-5amine, respectively, are obtained.

EXAMPLE 24

5-Methoxy-8-phenylethyl-2-propyl-8H-pyrazolo[4',3':5,6]-pyrido[3,4-e][1,2,4]triazolo[1,5-a]pyrimidine By substituting 1-phenylethyl-4-hydrazino-1H-pyrazolo-[3,4-b]pyridine-5-carboxylic acid, methyl ester for the 1-ethyl-4-hydrazino-1H-pyrazolo[3,4-b]pyridine-5-carboxylic acid, ethyl ester and 1-ethoxybutylidene cyanamide for the ethoxymethylene cyanamide in part a of the procedure of Example 1 (a), (b) then proceeding as in Example 5, 2-propyl-8-phenylethyl-4H-pyrazolo[4',3':5,6]pyrido[3,4-e][1,2,4]-triazolo[3,2-b]pyrimidin-5(8H)-one, 5-chloro-8-phenylethyl-2-propyl-8H-pyrazolo[4',3':5,6]pyrido[3,4-e][1,2,4]triazolo-[1,5-a]pyrimidine and 5-methoxy-8-phenylethyl-2-propyl-8H-pyrazolo[4',3':5,6]pyrido[3,4-e][1,2,4]triazolo[1,5-a]-pyrimidine, respectively, are obtained.

EXAMPLE 25

N,N,8-Triethyl-2-phenyl-8H-pyrazolo[4',3':5,6-]pyrido[3,4-e]-[1,2,4]triazolo[1,5-a]pyrimidin-5-amine By substituting α-ethoxybenzylidene cyanamide for the ethoxymethylene cyanamide in the procedure of Example 1 (a), (b) then proceeding as in Example 3, 8-ethyl-2-phenyl-4H-pyrazolo-[4',3':5,6]pyrido[3,4-e][1,2,4]triazolo[1,5-a]pyrimidine-5(8H)-one, 5-chloro-8-ethyl-2-phenyl-8H-pyrazolo[4',3':5,6]-pyrido[3,4-e][1,2,4]triazolo[1,5-a]pyrimidine and N,N,8-triethyl-2-phenyl-8H-pyrazolo[4',3':5,6]pyrido[3,4-e][1,2,4]-triazolo[1,5-a]pyrimidin-5-amine, respectively, are obtained.

EXAMPLE 26

8-Benzoyl-5-phenyloxy-8H-pyrazolo[4',3':5,6-]pyrido[3,4-e]-[1,2,4]triazolo[1,5-a]pyrimidine (a)
8-Furfuryl-5-phenyloxy-8H-pyrazolo[4',3':5,6]pyrido[3,4-e][1,2,4]triazolo[1,5-a]pyrimidine By substituting 4-hydrazino-1-furfurylpyrazolo-[3,4-b]pyridine-5-carboxylic acid, ethyl ester for the 1-ethyl-4-hydrazino-1H-pyrazolo[3,4-b]pyridine-5-carboxylic acid, ethyl ester in Example 1 a, 8-furfuryl-4H-pyrazolo-[4',3':5,6]pyrido[3,4-e][1,2,4]triazolo[1,5-a]pyrimidin-5(8H)-one is obtained. This compound is now processed as in Example 1 b and then as in Example 4, substituting phenol for the ethanol to obtain 8-furfuryl-5-phenyloxy-8H-pyrazolo[4',3':5,6]pyrido[3,4-e][1,2,4]triazolo-[1,5-a]pyrimidine.

(b)
5-Phenyloxy-8H-pyrazolo[4',3':5,6]pyrido[3,4-e][1,2,4]-triazolo[1,5-a]pyrimidine 0.01 mol. of 8-furfuryl-5-phenyloxy-8H-pyrazolo-[4',3':5,6]pyrido[3,4-e][1,2,4]triazolo[1,5-a]pyrimidine is heated in 50 ml. of diethyleneglycol dimethyl ether containing 0.01 mol. of selenium dioxide at reflux temperature with stirring for 2 hours. The mixture is filtered hot and evaporated to dryness. 5-Phenyloxy-8H- pyrazolo-[4',3':5,6]pyrido[3,4-e][1,2,4]triazolo[1,5-a]pyrimidine remains.

(c)
8-Benzoyl-5-phenyloxy-8H-pyrazolo[4',3':5,6]pyrido-[3,4-e][1,2,4]triazolo[1,5-a]pyrimidine 0.01 mol. of 5-phenyloxy-8H-pyrazolo[4',3':5,6-]pyrido-[3,4-e][1,2,4]triazolo[1,5-a]pyrimidine and 0.02 mol. of benzoyl chloride are stirred overnight in 50 ml. of dry pyridine at room temperature. On addition of 50 ml. of water, 8-benzoyl-5-phenyloxy-8H-pyrazolo[4',3':5,6]pyrido-[3,4-e][1,2,4]triazolo[1,5-a]pyrimidine is filtered off.

EXAMPLE 27

N-[3-(Dimethylamino)propyl]-8-(4-methylbenzoyl)-8H-pyrazolo-[4',3':5,6]pyrido[3,4-e][1,2,4]pyrimidin-5-amine By substituting 1-(4-methylbenzoyl)-4-hydrazino-1H-pyrazolo[3,4-b]pyridine-5-carboxylic acid, ethyl ester for the 1-ethyl-4-hydrazino-1H-pyrazolo[3,4-b]pyridine-5-carboxylic acid, ethyl ester in the procedure of Example 1, 8-(4-methylbenzoyl)-4H-pyrazolo[4',3':5,6-]pyrido[3,4-e]-[1,2,4]triazolo[1,5-a]pyrimidin-5(8H)-one, 5-chloro-8-(4-methylbenzoyl)-8H-pyrazolo[4',3':5,6]pyrido[3,4-e]-[1,2,4]triazolo[1,5-a]pyridimine and N-[3-(dimethylamino)propyl]-8-(4-methylbenzoyl)-8H-pyrazolo[4',3':5,6]pyrido-[3,4-e][1,2,4]triazolo[1,5-a]pyrimidin-5-amine, respectively, are obtained.

EXAMPLE 28

5-(2-Aminoethoxy)-6-methyl-8-ethyl-8H-pyrazolo[4',3':5,6]-pyrido[3,4-e][1,2,4]triazolo[1,5-a]pyrimidine By substituting the 8-ethyl-6-methyl-4H-pyrazolo-[4',3':5,6]pyrido[3,4-e][1,2,4]triazolo[1,5-a]pyrimidin-5(8H)-one obtained in Example 22 in the procedure of Example 7 but substituting 2-hydroxyethylamine for the 2-dimethylaminoethanol, 5-(2-aminoethoxy)-6-methyl-8-ethyl-4H-pyrazolo[4',3':5,6]pyrido[3,4-e][1,2,4]triazolo-[1,5-a]pyrimidine is obtained.

EXAMPLE 29

N-Phenyl-8-ethyl-8H-pyrazolo[4',3':5,6]pyrido[3,4-e]-[1,2,4]triazolo[1,5-a]pyrimidin-5-amine By substituting aniline for the 3-dimethylaminopropyl amine in the procedure of Example 1 (c), N-phenyl-8-ethyl-8H-pyrazolo[4',3':5,6]pyrido[3,4-e][1,2,4]triazolo[1,5-a]-pyrimidin-5-amine is obtained.

EXAMPLE 30

8-Ethyl-N-(2-methylphenyl)-8H-pyrazolo[4',3':5,6-]pyrido-[3,4-e][1,2,4]triazolo[1,5-a]pyrimidin-5-amine By substituting o-toluidine for the 3-dimethylaminopropylamine in the procedure of Example 1 c, 8-ethyl-N-(2-methylphenyl)-8H-pyrazolo[4',3':5,6]pyrido[3,4-e]-[1,2,4]triazolo[1,5-a]pyrimidin-5-amine is obtained.

EXAMPLE 31

N-(2-Dimethylaminoethyl-8,10-dimethyl-8H-pyrazolo[4',3':5,6]-pyrido[3,4-e][1,2,4]triazolo[1,5-a]pyrimidin-5-amine By substituting 2-dimethylaminoethylamine for the 3-dimethylaminopropyl-1-amine in part (c) and utilizing the 8,10-dimethyl-8H-pyrazolo[4',3':5,6]pyrido[3,4-e][1,2,4]-triazolo[1,5-a]pyrimidin-5(8H)-one of Example 18 instead of 8-ethyl-4H-pyrazolo[4',3':5,6]pyrido[3,4-e][1,2,4]triazolo-[1,5-a]pyrimidin-5(8H)-one in part (b) of the procedure of Example 1, N-(2-dimethylaminoethyl)-8,10-dimethyl-8H-pyrazolo[4',3,:5,6]pyrido[3,4-e][1,2,4]triazolo[1,5-a]-pyrimidin-5-amine is obtained.

EXAMPLE 32

N-(3-(Diethylaminopropyl)-8-phenyl-8H-pyrazolo[4',3':5,6]-pyrido[3,4-e][1,2,4]triazolo[1,5-a]pyrimidin-5-amine By substituting 3-diethylaminopropylamine for the 3-dimethylaminopropyl-1-amine in part c of the procedure of Example 1 and utilizing 8-phenyl-4H-pyrazolo[4',3',:5,6]-pyrido[4,3-d][1,2,4]triazolo[1,5-a]pyrimidin-5(8H)-one product of Example 21 instead of 8-ethyl-4H-pyrazolo[4',3':5,6]pyrido[3,4-e][1,2,4]triazolo[1,5-a]pyrimidin-5(8H)-one in part (b), N-3-(diethylaminopropyl)-8-phenyl-8H-pyrazolo[4',3':5,6]pyrido[3,4-e][1,2,4]triazolo[1,5-a]-pyrimidin-5-amine is obtained.

EXAMPLE 33

8-Ethyl-5-thiamorpholino-8H-pyrazolo[4',3':5,6-]pyrido-[3,4-e][1,2,4]triazolo[1,5-a]pyrimidine By substituting thiamorpholine for the 3-dimethylaminopropyl-1-amine in the procedure of Example 1, 8-ethyl-5-thiamorpholino-8H-pyrazolo[4',3':5,6-]pyrido-[3,4-e][1,2,4]triazolo[1,5-a]pyrimidine is obtained.

EXAMPLE 34

8-Ethyl-5-(piperazino)-8H-pyrazolo[4',3':5,6-]pyrido[3,4-e]-[1,2,4]triazolo[1,5-a]pyrimidine By substituting piperazine for the 3-dimethylaminopropylamine in the procedure of Example 1, 8-ethyl-5-(piperazino)-8H-pyrazolo[4',3':5,6]pyrido[3,4-e][1,2,4]-triazolo[1,5-a]pyrimidine is obtained.

EXAMPLE 35

8-Ethyl-5-(4-methyl-1-piperazinyl)-8H-pyrazolo[4',3':5,6]-pyrido[3,4-e][1,2,4]triazolo[1,5-a]pyrimidine By substituting 4-methylpiperazine for the 3-(dimethylamino)propylamine in the procedure of Example 1 (c), 8-ethyl-5-(4-methyl-1-piperazinyl)-8H-pyrazolo[4',3':5,6]-pyrido[3,4-e][1,2,4]triazolo[1,5-a]pyrimidine is formed.

EXAMPLE 36

8-Ethyl-5-(1-pyrrolidinyl)-8H-pyrazolo[4',3':5,6]-pyrido-[3,4-e][1,2,4]triazolo[1,5-a]pyrimidine By substituting pyrrolidine for 3-(dimethylamino)propylamine in the procedure of Example 1 (c), 8-ethyl-5-(1-pyrrolidinyl-8H-pyrazolo[4',3':5,6]pyrido[3,4-e][1,2,4]-triazolo[1,5-a]pyrimidine is obtained.

EXAMPLE 37

8-Ethyl-N-[3-(trifluoromethyl)phenyl]-8H-pyrazolo[4',3':5,6]-pyrido[3,4-e][1,2,4]triazolo[1,5-a]pyrimidin-5-amine 5.8 g. of 5-chloro-8-ethyl-8H-pyrazolo[4',3':5,6]-pyrido[3,4-e][1,2,4]triazolo[1,5-a]pyrimidine (0.02 mol.), 3 g. of triethylamine and 3.3. g. of 3-trifluoromethylaniline are refluxed in butyl alcohol for 24 hours with stirring. The solvent is removed in vacuo and the residue treated with 20 ml. of water and filtered off. Recrystallization from alcohol yields 8-ethyl-N-[3-(trifluoromethyl)phenyl]-8H-pyrazolo[4′,3′:5,6]pyrido[3,4-e][1,2,4]triazolo[1,5-a]-pyrimidin-5-amine.

EXAMPLE 38

8-Ethyl-8H-pyrazolo[4′,3,:5,6]pyrido[3,4-e][1,2,4]triazolo-[1,5-a]pyrimidin-5-amine By substituting aqueous ammonia (30%) for the diethylamine in the procedure of Example 3, 8-ethyl-8H-pyrazolo-[4′,3′:5,6]pyrido[3,4-e][1,2,4]triazolo[1,5-a]pyrimidin-5-amine is obtained.

EXAMPLE 39

8-Ethyl-8H-pyrazolo[4′,3′:5,6]pyrido[3,4-e][1,2,4]-triazolo[1,5-a]pyrimidine-5-thiol 5.6 g. of 5-chloro-8-ethyl-8H-pyrazolo[4′,3′:5,6]-pyrido[3,4-e][1,2,4]triazolo[1,5-a]pyrimidine (0.02 mol.) are dissolved in 100 ml. of dimethylformamide. 2 g. of powdered sodium sulfide are added and the mixture is stirred for 1 hour. After this time, the solution is carefully acidified with acetic acid. 8-Ethyl-8H-pyrazolo[3′,4′:5,6]pyrido[3,4-e][1,2,4]triazolo[1,5-a]pyrimidine-5-thiol precipitates and is filtered off.

EXAMPLE 40

8-Ethyl-5-(1-pyrazolyl)-8H-pyrazolo[4′,3′:5,6]pyrido-[3,4-e][1,2,4]triazolo[1,5-a]pyrimidine By substituting pyrazole for the 3-(dimethylamino)-propylamine in the procedure of Example 1 (c), 8-ethyl-5-(1-pyrazolyl)-8H-pyrazolo[4′,3′:5,6]pyrido[3,4-e][1,2,4]-triazolo[1,5-a]pyrimidine is obtained.

EXAMPLE 41

8-Ethyl-5-(dihydropyridazin-1-yl)-8H-pyrazolo[4′,3′:5,6]-pyrido[3,4-e][1,2,4]triazolo[1,5-a]pyrimidine By substituting dihydropyridazine for the 3-(dimethylamino)propylamine in the procedure of Example 1 (c), 8-ethyl-5-(dihydropyridazin-1-yl)-8H-pyrazolo[4′,3′:5,6]pyrido[3,4-e]-[1,2,4]triazolo[1,5-a]pyrimidine is obtained.

EXAMPLE 42

The following ingredients are used to make 1,000 200 mg. tablets each containing 100 mg. of active ingredient:

| | | |
|---|---|---|
| N-[3-(Dimethylamino)propyl]-8-ethyl-8H-pyrazolo[4′,3′:5,6]pyrido[3,4-e]-[1,2,4]triazolo[1,5-a]pyrimidine-5-amine | 100 | gm. |
| Polyvinyl pyrrolidone | 7.5 | gm. |
| Lactose | 20 | gm. |
| Magnesium stearate | 3.5 | gm. |
| Corn starch | 17.5 | gm. |
| Avicel (microcrystalline cellulose) | 51.5 | gm. |

The medicament and lactose are thoroughly admixed. The polyvinyl pyrrolidone is dissolved in ethanol USP to make a 30% solution. This solution is used to granulate the mixture of medicament and lactose. The granulation is passed through a No. 16 screen and air dried. The dried granulation is then passed through a No. 20 screen. To the screened granulate are added the magnesium stearate, Avicel and the corn starch and the mixture is blended. The blend is then compressed into 200 mg. tablets on a standard concave punch. The tablets are then veneer coated with methyl cellulose in a spray pan.

What is claimed is:

1. A compound of the formula

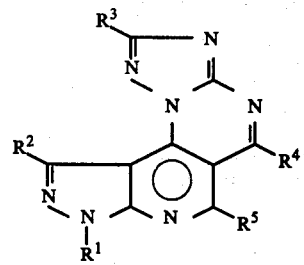

wherein $R^1$ is hydrogen, lower alkyl, phenyl, phenyl-lower alkylene, benzoyl or substituted benzoyl wherein the benzoyl substituent is one or two halogens, lower alkyl or trifluoromethyl groups;

$R^2$ is hydrogen, lower alkyl or phenyl;

$R^3$ is hydrogen, lower alkyl, phenyl, lower alkylthio or lower alkylsulfinyl;

$R^4$ is unsubstituted or substituted pyrrolidino, morpholino, thiamorpholino, piperidino, pyrazolyl, dihydropyridazinyl or piperazinyl wherein the heterocycle substituent is lower alkyl or hydroxy-lower alkylene;

$R^5$ is hydrogen or lower alkyl; and physiologically acceptable acid addition salts thereof.

2. A compound as in claim 1 wherein $R^1$, $R^2$ and $R^5$ each is hydrogen or lower alkyl; $R^3$ is hydrogen, lower alkyl or lower alkylthio; $R^4$ is piperidino, morpholino or 4-methylpiperazino.

3. A compound as in claim 1 wherein $R^2$, $R^3$ and $R^5$ each is hydrogen.

4. A compound as in claim 3 wherein $R^1$ is ethyl and $R^4$ is piperidino.

5. A compound as in claim 3 wherein $R^1$ is ethyl and $R^4$ is 4-methylpiperazino.

6. A compound as in claim 1 wherein $R^1$ is isopropyl, $R^2$ and $R^5$ each is hydrogen, $R^3$ is ethyl and $R^4$ is morpholino.

7. An anti-infammatory composition comprising about 10 to 300 mg. of a compound of claim 1 and a physiologically acceptable carrier therefor.

8. A method for treating inflammatory conditions which comprises administering to a mammal suffering therefrom a composition comprising about 10 to 300 mg. of a compound of claim 1 and a physiologically acceptable carrier therefor.

* * * * *